United States Patent
Shearer (10) Patent No.: US 9,468,370 B1
(45) Date of Patent: Oct. 18, 2016

(54) INSTRUMENT FOR MEASURING NEAR POINT OF CONVERGENCE AND/OR NEAR POINT OF ACCOMMODATION

(71) Applicants: Charles Shearer, Granger, IN (US); Bertec Corporation, Columbus, OH (US)

(72) Inventor: Charles Shearer, Granger, IN (US)

(73) Assignee: Bertec Corporation, Columbus, OH (US)

( * ) Notice: Subject to any disclaimer, the term of this patent is extended or adjusted under 35 U.S.C. 154(b) by 66 days.

(21) Appl. No.: 14/509,928

(22) Filed: Oct. 8, 2014

Related U.S. Application Data (60) Provisional application No. 61/888,615, filed on Oct. 9, 2013.

(51) Int. Cl.
*A61B 3/02* (2006.01)
*A61B 3/024* (2006.01)

(52) U.S. Cl.
CPC .................................... *A61B 3/024* (2013.01)

(58) Field of Classification Search
CPC ... A61B 3/0091; A61B 3/0083; A61B 3/154
USPC ......................................................... 351/208
See application file for complete search history.

(56) References Cited

U.S. PATENT DOCUMENTS

| | | | | |
|---|---|---|---|---|
| 4,968,131 | A * | 11/1990 | Lewis | A61B 3/032 351/239 |
| 2009/0153796 | A1* | 6/2009 | Rabner | A61B 3/0091 351/201 |
| 2015/0085252 | A1* | 3/2015 | Fujimura | A61B 3/15 351/208 |

FOREIGN PATENT DOCUMENTS

| | | | | |
|---|---|---|---|---|
| JP | WO 2013164943 A1 * | 11/2013 | | A61B 3/15 |

* cited by examiner

*Primary Examiner* — Mahidere Sahle
(74) *Attorney, Agent, or Firm* — The Law Office of Patrick F. O'Reilly III, LLC (57) ABSTRACT

An instrument for measuring near point of convergence (NPC) and/or near point of accommodation (NPA) is disclosed herein. The instrument includes at least one visual target disposed on or in the instrument, the at least one visual target viewable by a subject that is facing the instrument; a distance measuring device configured to emit one or more output signals that are representative of a distance between a surface of the instrument and a body surface of the subject spaced apart from the surface of the instrument; and a processing device operatively coupled to the distance measuring device, the processing device configured to receive the one or more output signals that are output by the distance measuring device and to calculate the distance between the surface of the instrument and the body surface of the subject spaced apart from the surface of the instrument using the one or more output signals.

18 Claims, 5 Drawing Sheets

SCALE 1 : 1
FIG. 4A

FIG. 5

INSTRUMENT FOR MEASURING NEAR POINT OF CONVERGENCE AND/OR NEAR POINT OF ACCOMMODATION

CROSS-REFERENCE TO RELATED APPLICATIONS

This patent application claims priority to, and incorporates by reference in its entirety, U.S. Provisional Patent Application No. 61/888,615, entitled "Instrument for Measuring Near Point of Convergence and Near Point of Accommodation", filed on Oct. 9, 2013.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to an instrument for vision testing. More particularly, the invention relates to an instrument for measuring near point of convergence (NPC) and near point of accommodation (NPA).

2. Background

Near point of convergence (NPC) is measured by bringing an object close to a user's eyes, and measuring the distance from the eyes at which the user begins to see double. Near point of accommodation (NPA) is measured by bringing an object close to a user's eyes, and measuring the distance from the eyes at which the object appears blurry to the user. Presently, devices for measuring NPC and NPA rely on manual measurements, recording and the use of crude tools. As such, an improved instrument for measuring NPC and NPA is needed.

BRIEF SUMMARY OF EMBODIMENTS OF THE INVENTION

Accordingly, the present invention is directed to an instrument for measuring near point of convergence (NPC) and/or near point of accommodation (NPA) that substantially obviates one or more problems resulting from the limitations and deficiencies of the related art.

In accordance with one or more embodiments of the present invention, there is provided an instrument for measuring near point of convergence (NPC) and/or near point of accommodation (NPA). The instrument includes at least one visual target disposed on or in the instrument, the at least one visual target viewable by a subject that is facing the instrument; a distance measuring device, the distance measuring device configured to emit one or more output signals that are representative of a distance between a surface of the instrument and a body surface of the subject spaced apart from the surface of the instrument; and a processing device operatively coupled to the distance measuring device, the processing device configured to receive the one or more output signals that are output by the distance measuring device and to calculate the distance between the surface of the instrument and the body surface of the subject spaced apart from the surface of the instrument using the one or more output signals.

In yet a further embodiment, the at least one visual target comprises a first visual target in the form of a single-colored light emitting device or a multi-colored light emitting device.

In still a further embodiment, the at least one visual target further comprises a second visual target having a plurality of spaced-apart light emitting devices, each of the plurality of spaced-apart light emitting devices configured to emit a color of light that is different from one another.

In yet a further embodiment, the at least one visual target further comprises a third visual target in the form of one or more optotypes having one or more configurations that are capable of being identified by the subject.

In still a further embodiment, at least one of the first visual target and the second visual target comprises one or more light-emitting diodes.

In yet a further embodiment, the distance measuring device comprises a range detector with a transmitter portion for emitting an ultrasonic or infrared pulse and a receiver portion for receiving the ultrasonic or infrared pulse after it is reflected off the body portion of the subject.

In still a further embodiment, the processing device is in the form of a microprocessor.

In yet a further embodiment, the instrument further comprises a visual display device operatively coupled to the processing device, the visual display device configured to display the distance calculated by the processing device to a user of the instrument.

In still a further embodiment, the visual display device comprises a liquid-crystal display (LCD).

In yet a further embodiment, the instrument further comprises a housing, the at least one visual target and the distance measuring device being mounted on the housing, and the processing device being disposed within the housing.

In still a further embodiment, the instrument further comprises at least one input device operatively coupled to the processing device, the at least one input device configured to receive an input from a user and to output one or more input signals in response to the input from the user, the processing device further configured to receive the one or more input signals that are output by the at least one input device and to record the calculated distance in a memory of the processing device.

In yet a further embodiment, the instrument further comprises one or more program selection buttons configured to enable a user to selectively choose between a plurality of different precompiled programs loaded on the instrument, a first of the plurality of different precompiled programs configured to execute a first test for determining a diplopia distance at which the subject sees a double image of the visual target, and a second of the plurality of different precompiled programs configured to execute a second test for determining an accommodation threshold distance at which the subject sees a blurry image of the visual target precluding an accurate identification of the visual target.

In still a further embodiment, the instrument further comprises at least one of a wireless data interface or a wired data interface operatively coupled to the processing device, the wireless data interface or the wired data interface configured to operatively couple the instrument to a remote electronic device so that data stored in the instrument is capable of being transmitted to the remote electronic device.

In yet a further embodiment, the instrument further comprises an auditory output device operatively coupled to the processing device, the auditory output device configured to emit a tone which varies in pitch as the instrument approaches the subject, the pitch of the tone emitted by the auditory output device steadily increasing from low to high as the instrument is moved closer to the subject.

In accordance with one or more other embodiments of the present invention, there is provided an instrument for measuring near point of convergence (NPC) and/or near point of accommodation (NPA). The instrument including at least one visual target disposed on or in the instrument, the at least one visual target viewable by a subject that is facing the instrument; a distance measuring device, the distance measuring device configured to emit one or more output signals that are representative of a distance between a surface of the instrument and a body surface of the subject spaced apart from the surface of the instrument; at least one input device, the at least one input device configured to receive an input from a user and to output one or more input signals in response to the input from the user; and a processing device operatively coupled to the distance measuring device and the at least one user input device, the processing device configured to receive the one or more output signals that are output by the distance measuring device and to calculate the distance between the surface of the instrument and the body surface of the subject spaced apart from the surface of the instrument using the one or more output signals, the processing device further configured to receive the one or more input signals that are output by the at least one input device and to record the calculated distance in a memory of the processing device.

In a further embodiment of the present invention, the at least one visual target comprises a first visual target in the form of a single-colored light emitting device or a multi-colored light emitting device.

In yet a further embodiment, the at least one visual target further comprises a second visual target having a plurality of spaced-apart light emitting devices, each of the plurality of spaced-apart light emitting devices configured to emit a color of light that is different from one another.

In still a further embodiment, the at least one visual target further comprises a third visual target in the form of one or more optotypes having one or more configurations that are capable of being identified by the subject.

In accordance with yet one or more other embodiments of the present invention, there is provided a method for measuring near point of convergence (NPC) and/or near point of accommodation (NPA) of a subject. The method comprising the steps of: (i) providing an instrument; (ii) positioning the instrument at an initial distance from the front of the head of the subject; (iii) displaying, by using the instrument, the at least one visual target to the subject so that the subject is able maintain his or her gaze on the at least one visual target; (iv) gradually advancing the instrument towards the front of the head of the subject while the distance between the surface of the instrument and the front of the head of the subject is calculated by the processing device of the instrument; (v) stopping the advancement of the instrument towards the front of the head of the subject when a point is reached at which the subject either sees a double image of the visual target or the subject sees a blurry image of the visual target precluding an accurate identification of the visual target; and (vi) determining and recording, by using the instrument, either a diplopia distance which corresponds to the point at which the subject sees the double image of the visual target or an accommodation threshold distance at which the subject sees the blurry image of the visual target precluding the accurate identification of the visual target. The instrument includes at least one visual target disposed on or in the instrument, the at least one visual target viewable by a subject that is facing the instrument; a distance measuring device, the distance measuring device configured to emit one or more output signals that are representative of a distance between a surface of the instrument and a front of a head of a subject spaced apart from the surface of the instrument; and a processing device operatively coupled to the distance measuring device, the processing device configured to receive the one or more output signals that are output by the distance measuring device and to calculate the distance between the surface of the instrument and the front of the head of the subject spaced apart from the surface of the instrument using the one or more output signals;

In a further embodiment of the present invention, the method further comprises performing an additional test, which includes the additional steps of: (vii) gradually advancing the instrument towards the front of the head of the subject until a first point is reached at which the subject sees a double image of the visual target; (viii) stopping the advancement of the instrument upon reaching the first point, and then subsequently gradually moving the instrument away from the front of the head of the subject until a second point is reached at which the subject no longer sees the double image of the visual target; and (ix) determining and recording, by using the instrument, a recovery distance which corresponds to the point at which the subject no longer sees the double image of the visual target.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same parts are always denoted using the same reference characters so that, as a general rule, they will only be described once.

DETAILED DESCRIPTION OF EMBODIMENTS OF THE INVENTION

In one or more embodiments, an instrument suitable for measuring NPC and NPA is provided. The illustrative instrument described herein includes a housing which carries a variety of electronics. The electronics include a range detector for measuring the distance between the instrument and the subject. The electronics also include a variety of visual targets, such as LEDs, which a subject looks at during the tests. The electronics also include a computer chip which stores data and controls the various attached systems. The illustrative instrument described herein is suitable for administering tests for NPC and NPA.

In accordance with an illustrative embodiment, an instrument 20 for digitally measuring both near point of convergence (NPC) and near point of accommodation (NPA) is shown in FIGS. 1-4C. The instrument includes a body formed from a front face plate 1 and a back face plate 7 (see e.g., FIG. 1). The front face plate 1 (see FIGS. 4A-4C) and the back face plate 7 (see FIGS. 3A-3C) together define a cavity which houses a variety of electronics, including a screen 8, a range detector 2, a system chip 9, a battery 10, and various targets and switches. As an example of one such switch, the instrument 20 may comprise a power switch 13 (e.g., a medium rocker switch—see e.g., FIG. 2B) for turning the device "on" and "off". These elements carried within the instrument are described in greater detail below. In one exemplary embodiment, the battery 10 may comprise a 9-volt battery.

In another embodiment, rather than using the front face plate 1 and the back face plate 7 illustrated in the figures for the housing of the instrument 20, the instrument 20 may comprise an alternative electronics enclosure with split sides and internal supports for accommodating a printed circuit board (PCB) mounted therein. The alternative electronics enclosure may comprise a battery compartment to accommodate a 9-volt battery, and may be fabricated from a suitable polymeric material or plastic, such as acrylonitrile butadiene styrene (ABS). In an exemplary embodiment, the alternative electronics enclosure may have an overall length of approximately 120 millimeters (mm), an overall width of approximately 60 millimeters (mm), and overall height of approximately 25 millimeters (mm). Although, it is to be understood that the invention is in no way limited to these particular dimensions. Rather, the invention may be practiced using any other suitable dimensions without departing from the spirit and scope of the appended claims.

The instrument 20 utilizes ultrasonic and/or infrared signals to measure the proximity of the instrument 20 to the bridge of the nose and/or forehead of a subject as the instrument 20 is moved to a given position relative the subject. The instrument 20 includes a range detector 2 which is suitable for emitting an ultrasonic or infrared pulse which bounces off the structure of the face or forehead of the subject and returns to a receiver portion of the range detector 2. The round-trip travel time of the pulse from range detector 2 is used to calculate the distance between the instrument 20 and the face or forehead of the subject. In one or more embodiments, the range detector 2 may comprise an ultrasonic range detector module with an emitter portion and receiver portion.

In one or more embodiments, the round-trip travel time of the pulse from range detector 2 may be used to calculate the distance (D) between the instrument 20 and the face or forehead of the subject in the following manner:

$$D = \frac{t * v_s}{2} \quad (1)$$

where:
t=round-trip travel time of the pulse from the range detector emitter to the detector
$v_s$=velocity of sound (340 meters per second).

In an exemplary embodiment, the ultrasonic range detector module with an emitter portion and receiver portion may have a 5-volt supply voltage, a trigger pulse input (e.g., 10 microsecond transistor-transistor logic (TTL) pulse), an echo pulse output, a maximum range of approximately four (4) meters, a minimum range of approximately two (2) centimeters, and a measuring angle of approximately 15 degrees. In the exemplary embodiment, the emitter or transmitter portion of the ultrasonic range detector module may emit an 8 cycle burst of ultrasound at 40 kHz and raise its echo.

The instrument 20 includes a front face plate 1 having several targets thereon. These targets are preferably lights, such as LEDs, at which the subject can fix his gaze during a test. The instrument 20 is suitable for performing multiple tests on a subject. The first test utilizes a first target 3, which may be a tricolor light-emitting diode (LED). In one exemplary embodiment, the tricolor light-emitting diode (LED) may comprise a 10 mm RGB diffused LED. To perform the first test, the instrument 20 is placed a suitable distance from the front of the subject's head, such that the instrument 20 is beyond the distance where the subject will see double (at this distance, the user only sees a single LED 3). The instrument 20 is then moved toward the subject's head, and as the instrument 20 is moved the instrument measures the distance between the instrument and the subject's head. As this distance decreases, the color of the first target 3 proceeds through a series of color changes, for instance, the first target may start red, change to yellow, and finally change to green as it moves closer to the subject's head. The purpose of the color change of the first target 3 is to make the first target 3 more interesting, keeping the subject's attention during the test. Alternatively, the instrument may be configured such that the first target remains a constant color throughout the test. When the instrument 20 reaches a point where the user indicates that they see double (e.g., the user sees two LEDs 3), a button 14 is pressed which is connected to a piezo element 11 (see FIG. 1), which in turn is connected to system chip 9 which is suitable for recording, storing, and processing information from the various systems in the instrument 20. In one exemplary embodiment, the button 14 may comprise a momentary pushbutton switch (e.g., 12 mm square momentary pushbutton switch—see e.g., FIG. 2D). The range detector 2 and the button 14 are both in electrical communication with the chip 9 which instructs the range detector 2 to measure the distance between the instrument 20 and the subject, and records and stores this information on the chip 9. The chip 9 is also connected to a display 8 which displays the recorded distance. In one or more exemplary embodiments, the chip 9 of the instrument 20 may comprise a central control board or microcontroller with a central processing unit (CPU) or microprocessor, flash program memory, data memory, EEPROM data memory, and a plurality of input/output (I/O) ports. In an exemplary embodiment, the microcontroller may have a 20 MHz clock speed, 4K flash program memory, and an operating voltage range of 2.0V to 5.5V.

In an alternative exemplary embodiment, the microcontroller may have a 16 MHz clock speed, 32 k flash memory, an input voltage of 7-12V, fourteen (14) digital input/output (I/O) pins (6 PWM outputs), and six (6) analog inputs.

The instrument 20 will also include a second target 5 which includes three single-colored LED's, one red, one green or blue, and one clear included on the front face 1 of the instrument 20. The second target 5 is suitable for use when administering a second test, administered to a subject wearing red/green or blue glasses (also known as anaglyph glasses), which second test can be used to determine if the subject is suppressing vision in an eye. Anaglyph glasses typically include a red lens over the right eye and a green or blue lens over the left eye. A red lens will block green light, and the green lens will block red light. If the red LED cannot be seen by the subject, this is an indication that vision in the subject's right eye (the eye associated with the green lens of the glasses) is suppressed. If the green or blue LED cannot be seen, this is an indication that the vision in the subject's left eye (the eye associated with the red lens of the glasses) is suppressed. The clear LED is viewable by both eyes when the subject wears the glasses, and is used for either testing or training purposes, similar to the Worth four dot test.

The instrument 20 includes a speaker 24 which is in electrical communication and is controlled by the chip 9. The speaker 24 emits a tone which varies in pitch as the instrument approaches the subject's head. The chip 9 is suitable for translating the distance measured by the range detector 2 into a particular pitch emitted by the speaker 24. In this way, during administration of the test, the instrument 20 begins at a position spaced away from the subject's head, and as the instrument is advanced toward the head the pitch of the tone increases from low to high.

Figure 1:
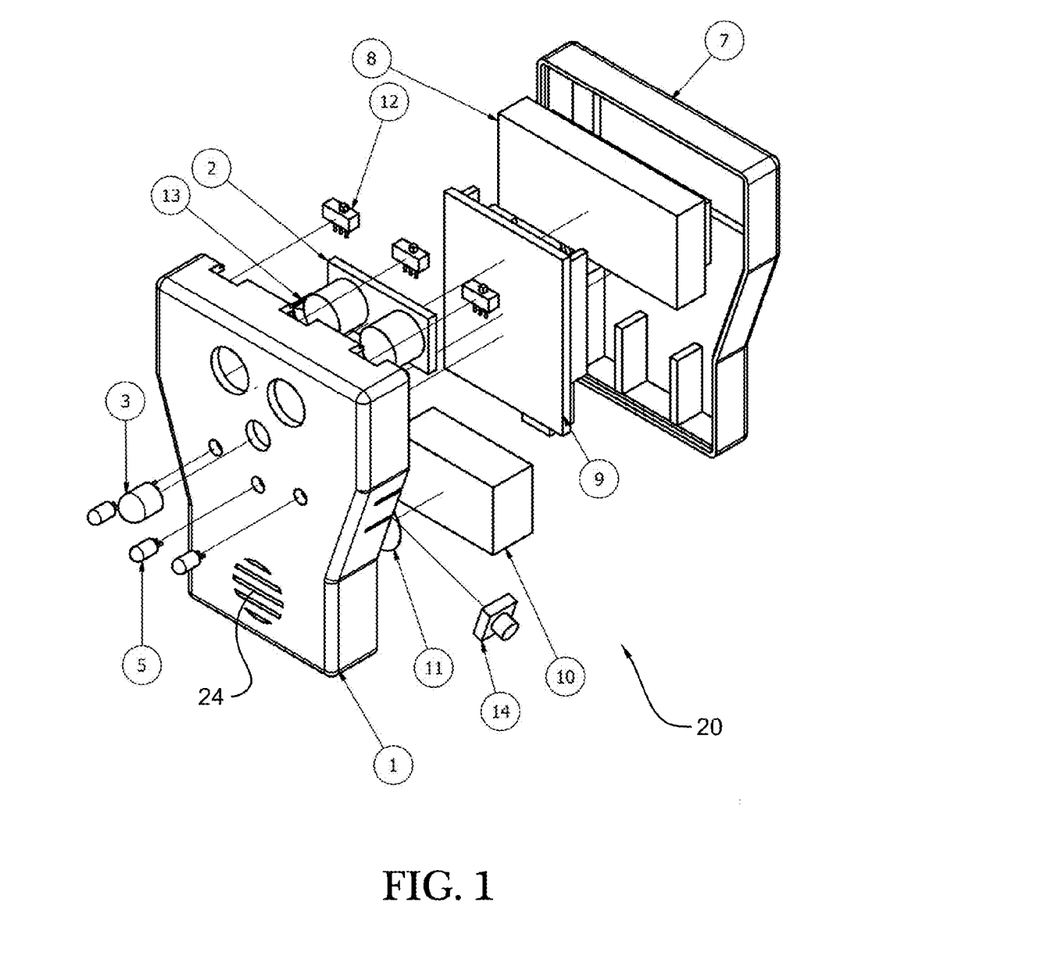
FIG. 1 is an exploded view of an instrument for measuring near point of convergence and near point of accommodation, according to one embodiment of the invention.
Figure 2A:
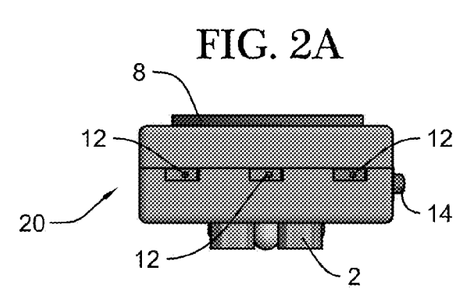
FIG. 2A is a top view of the instrument of FIG. 1.
Figure 2B:
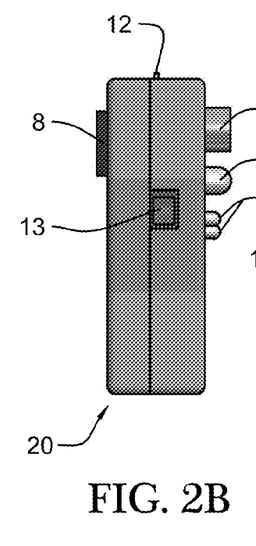
FIG. 2B is a left side view of the instrument of FIG. 1.
Figures 2C, 2D, 2E:
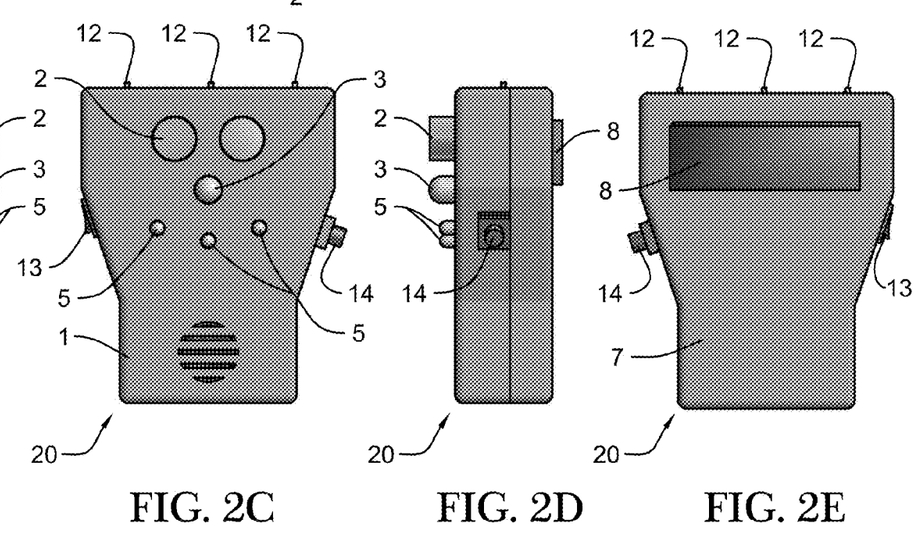
FIG. 2C is a front view of the instrument of FIG. 1.
FIG. 2D is a right side view of the instrument of FIG. 1.
FIG. 2E is a rear view of the instrument of FIG. 1.
Figure 3A:
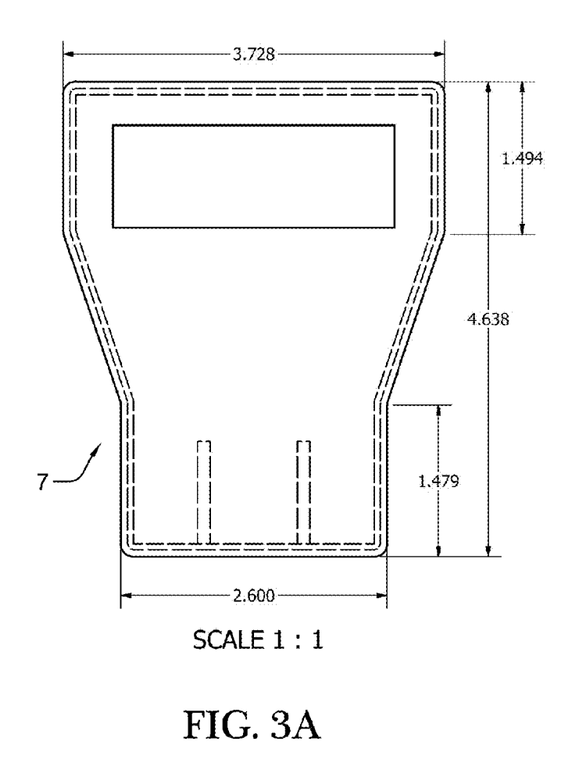
FIG. 3A is a rear view of the back plate of the instrument of FIG. 1.
Figure 3B:
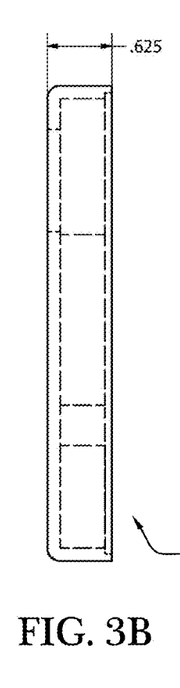
FIG. 3B is a side view of the back plate of the instrument of FIG. 1.
Figure 3C:
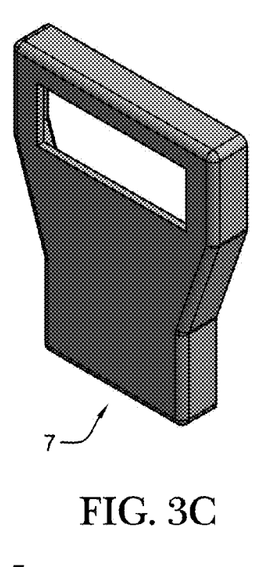
FIG. 3C is a perspective view of the back plate of the instrument of FIG. 1.
Figure 4A:
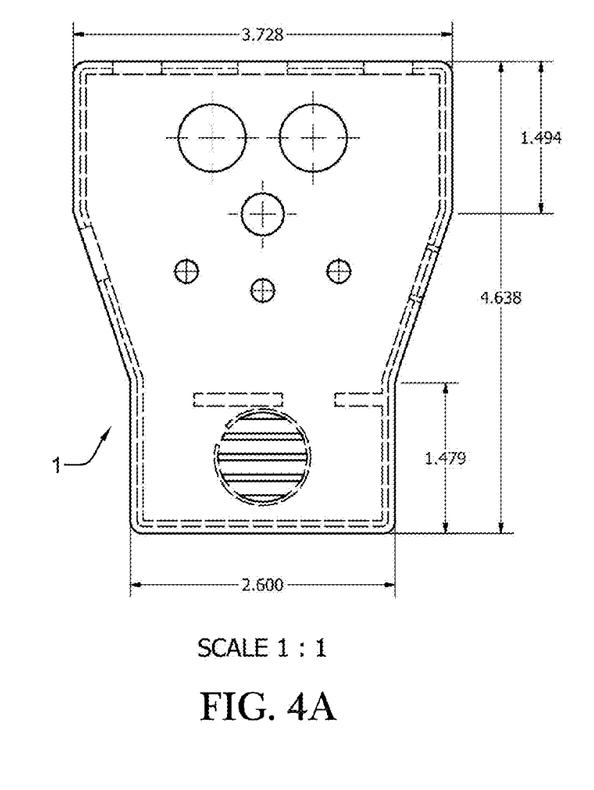
FIG. 4A is a front view of the face plate of the instrument of FIG. 1.
Figures 4B, 4C:
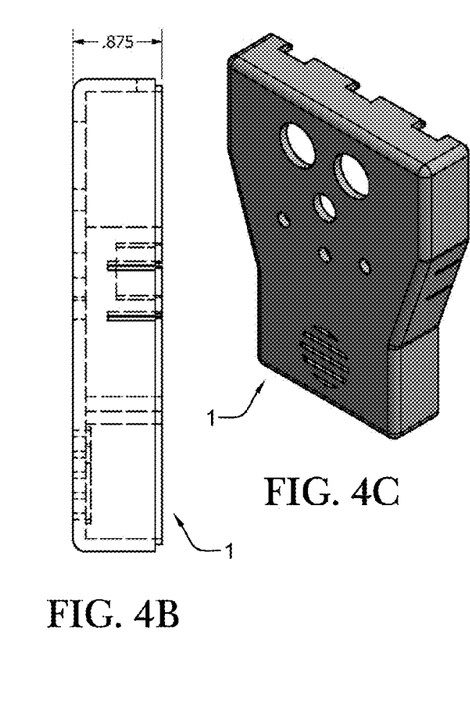
FIG. 4B is a side view of the face plate of the instrument of FIG. 1.
FIG. 4C is a perspective view of the face plate of the instrument of FIG. 1.

The instrument 20 includes a display screen 8 on the back face plate 7 (see e.g., FIG. 2E). As the various tests are administered, the screen 8 displays the distance of the instrument 20 to the subject (such as in inches or centimeters). In an exemplary embodiment, the display screen 8 may comprise a serial liquid crystal display (LCD) module. The button 14 is included on the instrument 20. When the button 14 is pressed, the instrument 20 will electronically store the distance between the instrument 20 and the subject's head at that point in time as measured by the range detector 2. During the administration of a test, the subject will be instructed to indicate when they notice a particular occurrence relative to one or more of the targets, such as when they experience double vision or suppression. Alternatively, the button 14 may be pressed when the person performing the test notices either that the subject's eyes converge, or that the subject's eyes stop converging.

The instrument 20 includes a wireless transmitter which is suitable for wirelessly transmitting data stored in the instrument to another device, such as a computer, a smartphone, or other suitable device. In one instance, the wireless transmitter is integrated with the chip 9, in any case, the wireless transmitter is in electrical communication with, and is controlled by, the chip 9. The wireless transmitter utilizes one or more wireless communication technologies which are common in the market, such as WiFi, Bluetooth and/or near field communication (NFC). The instrument 20 also includes a port (not shown) which is suitable for establishing a wired connection between the chip 9 and a computer, smartphone or other suitable device. Further, the instrument 20 also includes a compact removable memory chip (not shown) as are known, such as a removable flash memory storage device, for storing data collected on the chip 9 and transferring the data to a computer, smartphone or other suitable device.

The instrument 20 described herein is also suitable for measuring near point of accommodation (NPA). The front panel 1 of the instrument 20 includes a third target (see e.g., FIG. 5, Snellen box). The third target includes a series of symbols, such as the types of symbols which are generally included on an eye chart (such as a variation of a Snellen chart, Tumbling E chart, Landolt C chart, or other similar eye chart). During a test for NPA, the instrument 20 is positioned at a point spaced from the subject's head, with the front panel of the instrument 20 facing the subject. The subject views the front face 1 of the instrument 20 with the eye being tested, while the untested eye is covered with an occluding device. The instrument 20 is then moved slowly toward the subject until the subject reports that the third target is too blurry to read, the distance from the subject's head to the instrument is then recorded by pressing the button 14 on the instrument 20. The test is then repeated for the subject's other eye. Finally, the test is repeated a third time, but without either eye obstructed by the occluding device. The results of each iteration of the test are stored on the chip 9 and optionally displayed on the screen 8.

The instrument 20 is also suitable for measuring the recovery point of the subject's eyes. The recovery point is measured by having the subject focus on the first target 3 (a single LED) with both eyes as the instrument is advanced toward the subject's head. The subject indicates when the first target appears as two LEDs—when the subject is seeing double. The instrument 20 is then slowly moved away from the subject until the subject indicates that the first target appears as a single LED—the subject is no longer seeing double. This point where the subject is no longer seeing double is known as the recovery point. This point is measured by the range detector 2 when the user presses the button 14 and recorded and stored on the chip 9 of the instrument 20, and optionally displayed on the screen 8.

The instrument 20 includes one or more input devices. The input devices are suitable for collecting responses from a user. One such input device is the button 14, described herein. Another input device is one or more buttons 12 which may be positioned on the front face 1 or on a side thereof. The one or more buttons 12 allow a user to toggle between the different tests which may be administered by the instrument 20 (see e.g., FIGS. 2A and 2C). In one instance, a separate button 12 is provided to correspond with each of the tests administered by the instrument 20. In an exemplary embodiment, the instrument 20 may comprise three (3) buttons 12 in the form of three (3) single pole, double throw (SPDT) mini power switches, e.g., one for each test that may be administered. However, it is to be understood that, in other embodiments, four or more buttons 12 may be provided in order to accommodate four or more tests that are administered using the instrument 20 (as described below). In each case, the input devices are in electrical communication with the chip 9, which chip 9 in turn is in electrical communication with the various components of the instrument 20 and activates those components as described herein when a particular test is selected by the user using the input devices. Other input devices which are known are suitable for use with the instrument, including a touch screen, a microphone for receiving voice commands, a port for connecting an external keyboard or other input device, wireless control via a smartphone or other device, or any other known input device as is known and would be suitable for providing input signals to the chip 9 to initiate a given test.

Figure 5:
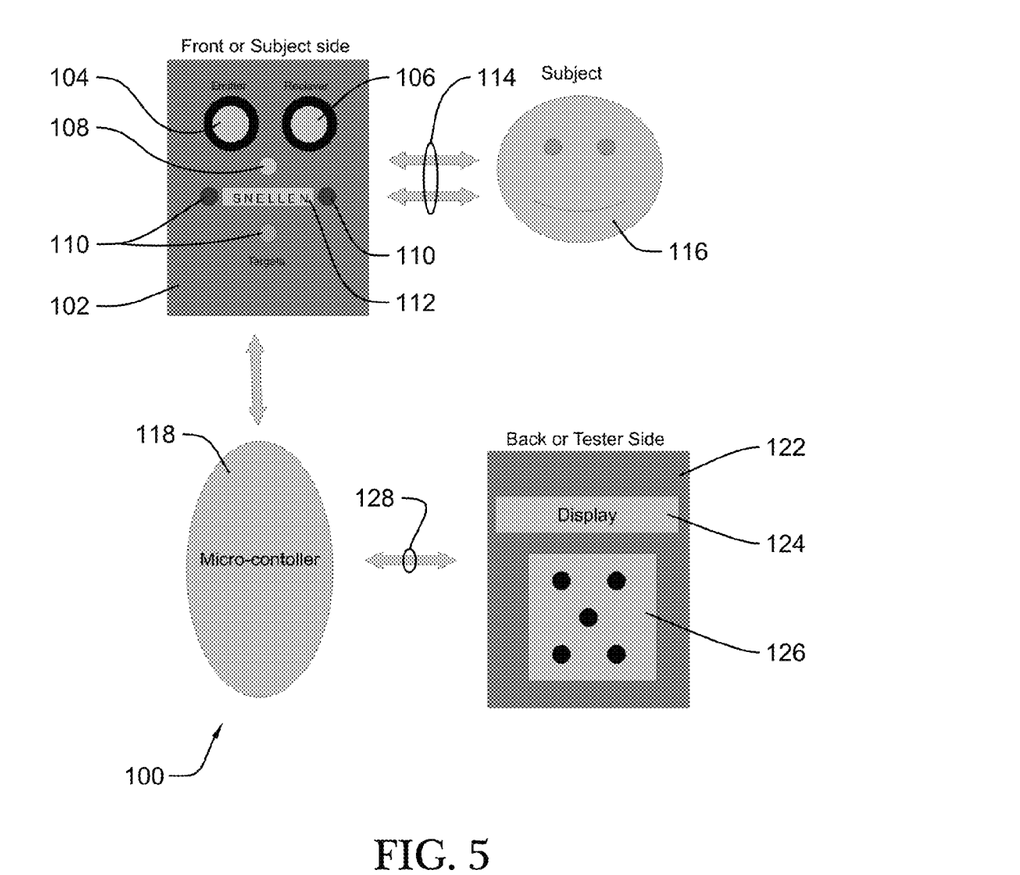
FIG. 5 is a schematic diagram of another instrument for measuring near point of convergence and near point of accommodation, according to an alternative embodiment of the invention.

With reference to the schematic diagram 100 of FIG. 5, another illustrative embodiment of the instrument 20 will be described. As shown in this figure, the front face or subject side 102 of the instrument comprises the emitter 104 and the receiver 106 of the ultrasonic range detector module, a first target 108 (i.e., similar to target 3 described above), a plurality of second targets 110 (i.e., similar to second targets 5 described above), and a third target 112 comprising a series of symbols, such as Snellen chart symbols (i.e., see third target discussion above). In an exemplary embodiment, the series of symbols of the third target may comprise a string of letters, such as "E B T C M B L A" and "N G O V M P L E", which the subject is asked to identify during the test. As diagrammatically indicated by the arrows 114 in FIG. 5, the front face 102 of the instrument is visible to the subject 116 during the vision testing of him or her. Also, as diagrammatically represented by the downwardly directed arrow in FIG. 5, the components 104, 106, 108, 110, 112 that are disposed on the front face 102 of the instrument are all operatively coupled (i.e., electrically connected) to the microcontroller 118 of the instrument (refer to discussion of microcontroller above). Referring again to FIG. 5, it can be seen that the back face or tester side 122 of the instrument comprises the display screen 124 (i.e., similar to display 8 described above) and an arrangement of buttons 126 that are used to select and control the different modes of operation and tests. As diagrammatically indicated by the arrow 128 in FIG. 5, the display screen 124 and the arrangement of buttons 126 on the back face of the instrument are also operatively coupled (i.e., electrically connected) to the microcontroller 118 of the instrument. As shown in FIG. 5, the arrangement of buttons 126 may comprise five (5) or more individuals buttons (e.g., in some embodiments, the instrument 20 may six (6) buttons in lieu of five (5) buttons). The buttons in the arrangement of buttons 126 may be used for controlling any or all of the following functions of the instrument: (i) mode/test selection, (ii) intensity control of the targets (i.e., controlling the brightness of the light emitting devices), (iii) measuring and/or recording the distance between the instrument and the face or forehead of the subject, (iv) activating and deactivating the power of the instrument (i.e., the main power switch), (v) activating and deactivating the sound delivered through the speaker of the instrument, and (vi) activating the Worth 4 dot test.

Advantageously, the instrument 20 described herein is suitable for determining any one of the following four (4) measurements: (i) near point of convergence break (NPCb), (ii) near point of convergence recovery (NPCr), (iii) near point of accommodation blur (NPAb), and (iv) near point of accommodation recovery (NPAr). Although, it is to be understood that the instrument 20 is not limited to these four (4) particular measurements. Rather, it is suitable for making other eye-related measurements as well.

The near point of convergence break (NPCb) is the point at which the subject can no longer converge or cross their eyes. This is tested by having the subject fixate on a small object or target as it is brought slowly towards his or her eyes. The subject is instructed keep the target single as long as possible, but to report when the target doubles. This is confirmed objectively by the tester watching their eyes. At the point where the subject can no longer cross their eyes, they should report two targets and the tester should notice the eye no longer making the converging eye movements. This is known as the near point of convergence (NPC) or near point of convergence break (NPCb).

The near point of convergence recovery (NPCr) is the point at which the eyes of the subject will regain convergence. This is tested by starting a target closer to the subject than their NPCb, and slowly moving it directly away from the eyes until they see one target instead of two. This is known as the recovery point of near point of convergence, or the NPCr.

The near point of accommodation blur (NPAb) is also tested using the instrument 20. This is tested by having the subject observe a line of 20/30 or 20/40 size letters (depending on the age of the subject and the testing protocol), calibrated for a test distance of 40 centimeters (cm). The letters are slowly brought toward the subject until they become too blurry to read. This is known as the near point of accommodation or near point of accommodation blur (NPAb).

The near point of accommodation recovery (NPAr) is additionally tested using the instrument 20. This test is started with the test letters being closer than the NPAb, and pulling it directly away from the subject, noting when they can first begin to read the letters. This is the recovery point of accommodation, or the NPAr.

The importance of these measurements has been well documented. They are especially important measurements pre-concussion and post-concussion. They also have been shown to be a key component in the areas of visually related learning problems and eye strain.

One application of the aforementioned tests is to determine if a subject is experiencing a concussion. For many subjects, NPC and NPA will differ when experiencing concussion symptoms, as compared to the NPC and NPA of the subject during normal, or unaffected, conditions. The present instrument 20 can be used to measure a NPC and NPA baseline, in other words, to take measurements of NPC and NPA when the subject is not experiencing concussion symptoms. The instrument 20 can then be used after an incident which has the potential to cause a concussion as one tool to determine if the subject is experiencing concussion symptoms.

More broadly, the instrument 20 is suitable for use to measure NPC and NPA as needed, and any reference to use for measuring concussions should not be read as limiting. For instance, measurement of NPC and NPA can also be used to detect reading problems.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. An instrument for measuring near point of convergence (NPC) and/or near point of accommodation (NPA), the instrument comprising:
   an instrument housing having a front face and a rear face disposed opposite to the front face;

at least one visual target disposed on or in the front face of the instrument housing, the at least one visual target viewable by a subject that is facing the front face of the instrument housing;

a distance measuring device disposed on or in the front face of the instrument housing, the distance measuring device configured to emit one or more output signals that are representative of a distance between a surface of the instrument and a body surface of the subject spaced apart from the surface of the instrument;

a processing device disposed within the instrument housing, the processing device operatively coupled to the distance measuring device, the processing device configured to receive the one or more output signals that are output by the distance measuring device and to calculate the distance between the surface of the instrument and the body surface of the subject spaced apart from the surface of the instrument using the one or more output signals; and a visual display device disposed on or in the rear face of the instrument housing, the visual display device operatively coupled to the processing device, and the visual display device configured to display the distance calculated by the processing device to a user of the instrument that is facing the rear face of the instrument housing.

2. The instrument according to claim 1, wherein the at least one visual target comprises a first visual target in the form of a single-colored light emitting device or a multi-colored light emitting device.

3. The instrument according to claim 2, wherein the at least one visual target further comprises a second visual target having a plurality of spaced-apart light emitting devices, each of the plurality of spaced-apart light emitting devices configured to emit a color of light that is different from one another, and each of the plurality of spaced-apart light emitting devices being spaced apart from one another by a portion of the instrument housing.

4. The instrument according to claim 3, wherein the at least one visual target further comprises a third visual target in the form of one or more optotypes having one or more configurations that are capable of being identified by the subject.

5. The instrument according to claim 3, wherein at least one of the first visual target and the second visual target comprises one or more light-emitting diodes.

6. The instrument according to claim 1, wherein the distance measuring device comprises a range detector with a transmitter portion for emitting an ultrasonic or infrared pulse and a receiver portion for receiving the ultrasonic or infrared pulse after it is reflected off the body portion of the subject.

7. The instrument according to claim 1, wherein the processing device is in the form of a microprocessor.

8. The instrument according to claim 1, wherein the visual display device comprises a liquid-crystal display (LCD).

9. The instrument according to claim 1, further comprising at least one input device operatively coupled to the processing device, the at least one input device configured to receive an input from a user and to output one or more input signals in response to the input from the user, the processing device further configured to receive the one or more input signals that are output by the at least one input device and to record the calculated distance in a memory of the processing device.

10. The instrument according to claim 1, further comprising one or more program selection buttons configured to enable a user to selectively choose between a plurality of different precompiled programs loaded on the instrument, a first of the plurality of different precompiled programs configured to execute a first test for determining a diplopia distance at which the subject sees a double image of the visual target, and a second of the plurality of different precompiled programs configured to execute a second test for determining an accommodation threshold distance at which the subject sees a blurry image of the visual target precluding an accurate identification of the visual target.

11. The instrument according to claim 1, further comprising at least one of a wireless data interface or a wired data interface operatively coupled to the processing device, the wireless data interface or the wired data interface configured to operatively couple the instrument to a remote electronic device so that data stored in the instrument is capable of being transmitted to the remote electronic device.

12. The instrument according to claim 1, further comprising an auditory output device operatively coupled to the processing device, the auditory output device configured to emit a tone which varies in pitch as the instrument approaches the subject, the pitch of the tone emitted by the auditory output device steadily increasing from low to high as the instrument housing is moved closer to the subject.

13. An instrument for measuring near point of convergence (NPC) and/or near point of accommodation (NPA), the instrument comprising:

an instrument housing having a front face and a rear face disposed opposite to the front face;

at least one visual target disposed on or in the front face of the instrument housing, the at least one visual target viewable by a subject that is facing the front face of the instrument housing;

a distance measuring device disposed on or in the front face of the instrument housing, the distance measuring device configured to emit one or more output signals that are representative of a distance between a surface of the instrument and a body surface of the subject spaced apart from the surface of the instrument;

at least one input device, the at least one input device configured to receive an input from a user and to output one or more input signals in response to the input from the user;

a processing device disposed within the instrument housing, the processing device operatively coupled to the distance measuring device and the at least one user input device, the processing device configured to receive the one or more output signals that are output by the distance measuring device and to calculate the distance between the surface of the instrument and the body surface of the subject spaced apart from the surface of the instrument using the one or more output signals, the processing device further configured to receive the one or more input signals that are output by the at least one input device and to record the calculated distance in a memory of the processing device; and a visual display device disposed on or in the rear face of the instrument housing, the visual display device operatively coupled to the processing device, and the visual display device configured to display the distance calculated by the processing device to a user of the instrument that is facing the rear face of the instrument housing.

14. The instrument according to claim 13, wherein the at least one visual target comprises a first visual target in the form of a single-colored light emitting device or a multi-colored light emitting device.

15. The instrument according to claim 14, wherein the at least one visual target further comprises a second visual target having a plurality of spaced-apart light emitting devices, each of the plurality of spaced-apart light emitting devices configured to emit a color of light that is different from one another, and each of the plurality of spaced-apart light emitting devices being spaced apart from one another by a portion of the instrument housing.

16. The instrument according to claim 15, wherein the at least one visual target further comprises a third visual target in the form of one or more optotypes having one or more configurations that are capable of being identified by the subject.

17. A method for measuring near point of convergence (NPC) and/or near point of accommodation (NPA) of a subject, the method comprising the steps of:

providing an instrument that includes:
- an instrument housing having a front face and a rear face disposed opposite to the front face;
- at least one visual target disposed on or in the front face of the instrument housing, the at least one visual target viewable by a subject that is facing the front face of the instrument housing;
- a distance measuring device disposed on or in the front face of the instrument housing, the distance measuring device configured to emit one or more output signals that are representative of a distance between a surface of the instrument and a front of a head of a subject spaced apart from the surface of the instrument; and
- a processing device disposed within the instrument housing, the processing device operatively coupled to the distance measuring device, the processing device configured to receive the one or more output signals that are output by the distance measuring device and to calculate the distance between the surface of the instrument and the front of the head of the subject spaced apart from the surface of the instrument using the one or more output signals;

positioning the instrument at an initial distance from the front of the head of the subject;

displaying, by using the instrument, the at least one visual target to the subject so that the subject is able maintain his or her gaze on the at least one visual target;

gradually advancing the instrument housing towards the front of the head of the subject while the distance between the surface of the instrument and the front of the head of the subject is calculated by the processing device of the instrument;

stopping the advancement of the instrument housing towards the front of the head of the subject when a point is reached at which the subject either sees a double image of the visual target or the subject sees a blurry image of the visual target precluding an accurate identification of the visual target; and determining and recording, by using the instrument, either a diplopia distance which corresponds to the point at which the subject sees the double image of the visual target or an accommodation threshold distance at which the subject sees the blurry image of the visual target precluding the accurate identification of the visual target.

18. The method according to claim 17, further comprising performing an additional test, which includes the additional steps of:

gradually advancing the instrument housing towards the front of the head of the subject until a first point is reached at which the subject sees a double image of the visual target;

stopping the advancement of the instrument housing upon reaching the first point, and then subsequently gradually moving the instrument housing away from the front of the head of the subject until a second point is reached at which the subject no longer sees the double image of the visual target; and determining and recording, by using the instrument, a recovery distance which corresponds to the point at which the subject no longer sees the double image of the visual target.

* * * * *